United States Patent [19]
Sherman et al.

[11] Patent Number: 4,857,533
[45] Date of Patent: Aug. 15, 1989

[54] METHOD OF TREATMENT FOR AUTOIMMUNE DISEASES

[75] Inventors: Fred P. Sherman, Hollywood; David C. Atkinson, Pembroke Pines, both of Fla.

[73] Assignee: Baker Cummins Pharmaceuticals, Inc., Miami, Fla.

[21] Appl. No.: 284,615

[22] Filed: Dec. 15, 1988

[51] Int. Cl.⁴ .............................. A61K 31/44
[52] U.S. Cl. ..................................... 514/282
[58] Field of Search ........................ 514/282

[56] References Cited

PUBLICATIONS

Chem. Abst. 100 (1984)-80084b-1.
Chem. Abst. 108 (1988)-143338a.
Rios et al., *Eur. J. Pharm.*, 96:277-289 (1983).
Kayser et al., *Proceedings of the Vth World Congress on Pain*, pp. 72-79 (Elsevier Science Publishers 1988).
Hargreaves et al., *Proceedings of the Vth World Congress on Pain*, pp. 55-60 (Elsevier Science Publishers 1988).

*Primary Examiner*—Stanley J. Friedman
*Attorney, Agent, or Firm*—Kirschstein, Ottinger, Israel & Schiffmiler

[57] ABSTRACT

A method of treating a human or animal patient suffering from an autoimmune disease comprises daily administration to such patient of from about 1 to about 100 mg of the narcotic antagonists nalmefene or naltrexone. The nalmefene or naltrexone may be administered in equally divided doses from one to four times daily, preferably by the oral route. Parenteral administration may be utilized where suitable.

10 Claims, No Drawings

METHOD OF TREATMENT FOR AUTOIMMUNE DISEASES

BACKGROUND OF THE INVENTION

1. Field of the Invention

The invention relates to methods of treating autoimmune diseases, e.g., systemic lupus erythematosus and rheumatoid arthritis.

2. Description of the Prior Art

Autoimmunity develops when an organism mounts an anti-self response, usually as a result of abnormalities of the afferent parts of the immune system which are involved in antigen-specific responses. Autoimmunity is a primary cause or secondary contributor in many diseases, usually as a result of the formation of autoantibodies by the immune system of the organism which attack its own cells. Such diseases include, for example, systemic lupus erythematosus, rheumatoid arthritis, autoimmune thyroiditis, autoimmune hemolytic anemia, and certain forms of progressive liver disease.

Systemic lupus erythematosus produces disturbances in more than one organ system with abnormalities in the immune system. Deposition of antigen-autoantibody complexes in tissues with resultant damage produces many of the clinical manifestations seen in lupus. These include arthritis with pain and swelling in both small and large joints, which may be confused with rheumatoid arthritis. Arthritis or arthralgia is seen in 55 percent of lupus patients. The classic "butterfly rash" which is an erythematous rash over the face and bridge of the nose is seen in 42 percent of lupus patients. Renal involvement secondary to deposition of antigen-antibody complexes producing glomerulonephritis is a major cause of morbidity and mortality in lupus patients. Cardiac involvement is seen in about half the lupus patients and also accounts for significant morbidity and mortality. Systemic lupus erythematosus may involve almost any organ system and confuse the physician as to the primary diagnosis.

Large numbers of autoantibodies which react with the nuclear and cytoplasmic constituents of cells are found in patients with systemic lupus. These antinuclear antibodies (ANA) are detected in 99 percent of lupus patients.

Lupus patients are often initially diagnosed as having rheumatoid arthritis, rheumatic fever, glomerulonephritis, lymphoma, scleroderma or tuberculosis before further evaluation eventually reveals the identity of their disease. The diagnosis of systemic lupus erythematosus can be made if any four or more of the following disorders or blood test results are present at any interval of observation: malar rash, discoid rash, photosensitivity, arthritis, serositis, renal disease, neurological disorder, hematologic disorder, immunologic disorder and high antinuclear antibody titer. E.M. Tan et al., *Arthritis Rheum.* 25:1271-1277 (1982).

At the present time there is no single effective therapy for systemic lupus. Treatment must be specifically tailored for the organ system or systems affected. Some of the pharmaceutical agents which are currently used include nonsteroidal anti-inflammatory drugs to treat the arthritis associated with lupus; antimalarials, which probably work by direct action on the immune system, to treat the arthritis, skin manifestations and fatigue of lupus; glucocorticoids, used for both their immunosuppressive and anti-inflammatory properties; and immunosuppressive and cytotoxic agents, generally used only when there is significant renal involvement which is unresponsive to glucocorticoids. See D. S. Pisetsky, *Advances in Rheumatology*, 70(2):337-352 (1986).

All of the currently practiced drug treatments for lupus have significant drawbacks. Apart from gastrointestinal disturbances, the nonsteroidal anti-inflammatory drugs may cause renal toxicity and therefore must be avoided particularly in lupus patients with renal involvement. The antimalarials may cause serious retinopathy which can occur several years after initiation of therapy. Chronic glucocorticoid therapy is associated with a number of pernicious side effects, including hypertension, excessive immunosuppression and CNS dysfunction. Immunosuppressive and cytotoxic agents can cause bone marrow depression and lead to serious infection.

Rheumatoid arthritis in its fully developed form is a symmetrical, inflammatory disease of the synovial lining of peripheral joints which leads to destructive changes. Although arthritis is the most frequent and prominent manifestation, this is a generalized disease involving many body systems.

Pathologically, rheumatoid arthritis is an inflammatory disease involving the immune system. Immune complexes (antigen/antibody) form within the joint and activate the complement system. White blood cells are then attracted into the synovial fluid. These cells phagocytose the immune complexes and in so doing release lysosomal enzymes and other chemical mediators of inflammation. Continued inflammation causes the synovium to proliferate and spread over the joint surface. The thickened synovial tissue, called pannus, releases enzymes which erode both cartilage and bone to cause permanent damage.

Rheumatoid arthritis is treated with many of the same pharmaceutical agents used in systemic lupus. Most patients initially receive nonsteroidal anti-inflammatory drugs, sometimes together with other analgesics. Where the disease is not adequately controlled with these agents, disease-modifying antirheumatic drugs, such as gold salts, D-penicillamine, antimalarial agents and cytotoxic agents, may be utilized. Ultimately, glucocorticoids may be administered, systemically or by the intraarticular route. Continuing therapy with any or all of the aforementioned categories of drugs can produce a variety of well-known adverse effects, and none of these drugs are significantly effective in achieving true remission of the disease in most patients.

It has been hypothesized that many of the manifestations of joint damage occurring in rheumatoid arthritis could be partly, if not largely, the result of damaging free oxygen radicals, large amounts of which are released together with powerful digestive enzymes into the arthritic joint by polymorphonuclear leukocytes undergoing "frustrated phagocytosis". These radicals have been shown to degrade DNA and hyaluronic acid, a major oxygen constituent of synovial fluid, and, to some extent, to degrade also collagen and elastin. Moreover, oxidants can activate latent collagenase, possibly by inactivating protease inhibitors, leading ultimately to cartilage destruction.

It is known that inflammatory cells such as polymorphonuclear leukocytes have opiate receptors. The endogenous opioid $\beta$-endorphin has been shown in vitro to stimulate superoxide radical production by human polymorphonuclear leukocytes via an opiate receptor. This superoxide production has been shown to be abolished by equimolar concentrations of the opiate antagonist naloxone. B.M. Sharp et al., *J. Pharm. Exp. Ther.*, 242(2):579–582 (1987). Naloxone has also been shown to inhibit in vitro the production of superoxide from human neutrophils stimulated with N-formyl-methionyl-leucyl-phenylalanine, which effect is not opiate receptor-mediated, nor is it the result of superoxide scavenging. Simpkins et al., *Life Sciences*, 37:1381–1386 (1985).

Systemically-administered naloxone has been shown to exert tissue-protective effects in a variety of experimental and clinical conditions in which the damaging effects of superoxide radicals and their derived oxygen species (hydrogen peroxide and the hydroxyl radical) are believed to play a major role. In particular, naloxone has been recently shown to have a protective effect on the ultrastructure of the ischemic canine kidney. H. K. Elkadi et al., *J. Surg. Res.*, 42:675–692 (1987).

Despite the foregoing, neither naloxone nor any other opioid antagonist has been disclosed heretofore as clinically useful in the treatment of the inflammatory manifestations of autoimmune diseases such as systemic lupus and rheumatoid arthritis. There has also been no suggestion that such antagonists might not only relieve inflammation but also reduce autoantibody levels to cause true remission in autoimmune diseases.

SUMMARY OF THE INVENTION

It is the object of the present invention to provide a method of treatment for autoimmune diseases which avoids the drawbacks and disadvantages of the prior art drug treatment methods while achieving dramatic symptomatic relief and reducing systemic autoantibody levels. In keeping with this object and others that will become apparent hereinafter, the present invention resides in the daily administration to patients suffering from autoimmune diseases, such as systemic lupus erythematosus and rheumatoid arthritis, of from about 1 to about 100 milligrams of either of the narcotic antagonists nalmefene or naltrexone. The oral route of administration is preferred for patient convenience, comfort and safety.

DETAILED DESCRIPTION OF THE INVENTION

Nalmefene (6-methylene-6-desoxy-N-cyclopropylmethyl-14-hydroxydihydronormorphine) is a long-acting, orally available, potent narcotic antagonist with pure antagonist activity. Apart from its utility in antagonizing the sedation, respiratory depression and other actions of opioid agents, nalmefene has also been found useful in treating diverse conditions such as hyperkinesia in children (U.S. Pat. No. 4,454,142), senile dementia (U.S. Pat. No. 4,511,570) and sudden infant death syndrome (U.S. Pat. No. 4,639,455), among others. Nalmefene has not hitherto been disclosed, however, as having any utility in the treatment of autoimmune diseases.

Naltrexone (N-cyclopropylmethyl-14-hydroxydihydromorphinone) is another orally available narcotic antagonist with pure antagonist activity. Naltrexone has additionally been disclosed as useful for inducing anorexia (U.S. Pat. Nos. 4,477,457; 4,478,840) and for treating shock (U.S. Pat Nos. 4,267,182; 4,434,168) but not for the treatment of autoimmune diseases.

The method of the present invention consists of the daily administration to human or animal patients suffering from an autoimmune disease, particularly systemic lupus or rheumatoid arthritis, of from about 1 to about 100 mg of nalmefene or naltrexone. The oral route of administration is preferred so that the patient can self-medicate safely and conveniently. Nalmefene and naltrexone, unlike certain other narcotic antagonists (e.g. naloxone), are highly effective and substantially bioavailable when administered orally. Nalmefene and naltrexone can be administered parenterally as well, however, for purposes of the present invention.

As used herein, the term "autoimmune disease" refers to any disease state or condition associated with the formation of autoantibodies reactive with the patient's own cells to form antigen-antibody complexes. The term "autoimmune disease" includes conditions which are not normally triggered by a specific external agent, e.g., systemic lupus erythematosus, rheumatoid arthritis, autoimmune thyroiditis and autoimmune hemolytic anemia, as well as those disorders which are triggered by a specific external agent, e.g., acute rheumatic fever.

In accordance with the present invention, nalmefene or naltrexone may be administered to patients suffering from an autoimmune disease in any conventional oral or parenteral dosage form. Oral dosage forms may include tablets, capsules, caplets, liquids, and the like, including generally from about 0.5 to about 50.0 mg of nalmefene or naltrexone per dosage unit together with suitable pharmaceutically-acceptable excipients, binders, sweeteners, coloring agents and other conventional additives. Parenteral dosage forms may include any conventional injectable solutions of nalmefene or naltrexone, for example an isotonic saline solution together with pharmaceutically-acceptable preservatives and buffers. The parenteral dosage forms generally contain from about 0.5 to about 50.0 mg of nalmefene or naltrexone and may be injected by the subcutaneous, intramuscular, intravenous or intra-articular routes.

By one preferred method, the nalmefene or naltrexone may be initially administered to patients in two daily doses of 1 or 2 mg each, for example for a one-week period, with gradual increments of 1 or 2 mg b.i.d. up to a maximum of 50 mg b.i.d.

The method of the present invention not only provides dramatic symptomatic relief for patients suffering from autoimmune diseases, for example systemic lupus patients, but has been found to reduce the patient's systemic autoantibody level, potentially leading to a true remission in the course of the disease.

Apart from systemic routes of administration, nalmefene or naltrexone may be administered to autoimmune-diseased patients locally at a diseased site—for example, injected intraarticularly in the case of rheumatoid arthritis patients. Nalmefene is particularly well-suited for both systemic and local use because of its long duration of action.

Although there may be no need to administer the nalmefene or naltrexone more than once or twice daily to achieve the result envisioned by the present invention, equally divided doses administered up to four times daily may be utilized. There have been few reports of any significant adverse effects with nalmefene or naltrexone therapy at the dosage levels proposed by the present invention, unlike many of the pharmaceutical agents which have been conventionally used to treat autoimmune diseases.

The following example provides a detailed illustration of the method of the present invention. This example is not intended to limit or restrict the scope of the invention in any way, and should not be construed as providing dosage forms, regimens or methods of administration which must be utilized exclusively to practice the invention.

EXAMPLE

A 64-year old female patient was diagnosed as suffering from systemic lupus erythematosus based on her symptomatology (small joint arthritis, butterfly rash, fatigue, depression and photosensitivity), her antinuclear antibody (ANA) titer and her C-reactive protein. She also suffered from interstitial cystitis, which is recognized as part of the lupus syndrome.

The patient was administered 1.0 mg tablets of nalmefene twice daily for seven days after which the dosage was increased in weekly increments of 1 mg b.i.d. until she was receiving 10 mg b.i.d.

When she reached a dosage level of 6 mg of nalmefene b.i.d. the patient noted marked reduction in her joint pain associated with less fatigue and an absence of depression. Her urinary symptoms of interstitial cystitis were also greatly improved by that stage. The patient's blood count, electrolytes, renal function, liver enzymes and clotting paramiters continued in the normal range even after four months of treatment, most of that time on the maintenance dose of 20 mg daily. The patient no longer required concomitant medications for her arthritis and was able to perform manual activities without pain. Her lupus symptoms improved markedly, with the exception of the butterfly rash.

With respect to the patient's laboratory tests, her ANA titer prior to nalmefene treatment was 1:160, which was reduced to 1:40 after a period at the maintenance dose of 10 mg b.i.d. The patient's C-reactive protein, which was strongly positive at the initiation of the study, was negative after nalmefene treatment.

It has thus been shown that there are provided methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims:

1. A method of treating a human or animal patient suffering from an autoimmune disease comprising the daily administration to the patient of from about 1 to about 100 mg of nalmefene or naltrexone.

2. A method according to claim 1 wherein said autoimmune disease is selected from the group consisting of systemic lupus erythematosus, rheumatoid arthritis, autoimmune thyroiditis, autoimmune hemolytic anemia, and acute rheumatic fever.

3. A method according to claim 2 wherein said autoimmune disease is selected from the group consisting of systemic lupus erythematosus and rheumatoid arthritis.

4. A method according to claim 1 wherein the nalmefene or naltrexone is administered to the patient orally.

5. A method according to claim 4 wherein the nalmefene or naltrexone is administered to the patient in an oral dosage form comprising a tablet, capsule, caplet or liquid containing from about 0.5 to about 50.0 mg of nalmefene.

6. A method according to claim 1 wherein the nalmefene or naltrexone is administered to the patient parenterally.

7. A method according to claim 6 wherein the nalmefene or naltrexone is administered to the patient by the subcutaneous, intramuscular, intravenous or intra-articular routes.

8. A method according to claim 1 wherein the nalmefene or naltrexone is administered to the patient from one to four times daily.

9. A method according to claim 8 wherein the nalmefene or naltrexone is administered to the patient from one to two times daily.

10. A method according to claim 9 wherein 1 mg of nalmefene or naltrexone is administered to a patient twice daily for an initial period, after which the dosage amount is gradually increased to a maximum of 50 mg twice daily.

* * * * *